(12) United States Patent
Liu et al.

(10) Patent No.: US 7,624,647 B2
(45) Date of Patent: Dec. 1, 2009

(54) SPRING SUPPORTED LOWER CLAMPER FOR DIRECT TENSILE TEST

(75) Inventors: Jianfeng Liu, Chengdu (CN); Jin Xu, Chengdu (CN); Heping Xie, Chengdu (CN)

(73) Assignee: Sichuan University, Chengdu, Si Chuan Province (CN)

( * ) Notice: Subject to any disclaimer, the term of this patent is extended or adjusted under 35 U.S.C. 154(b) by 117 days.

(21) Appl. No.: 11/931,162

(22) Filed: Oct. 31, 2007

(65) Prior Publication Data

US 2008/0276719 A1 Nov. 13, 2008

(30) Foreign Application Priority Data

Nov. 8, 2006 (CN) .......................... 2006 1 0022224

(51) Int. Cl.
*G01N 3/08* (2006.01)

(52) U.S. Cl. ...................................................... 73/831

(58) Field of Classification Search .................. 73/831, 73/856

See application file for complete search history.

(56) References Cited

U.S. PATENT DOCUMENTS

| | | | | |
|---|---|---|---|---|
| 2,488,279 A | * | 11/1949 | Fitzmaurice et al. | ........ 227/147 |
| 3,182,493 A | * | 5/1965 | Patterson et al. | ............... 73/831 |
| 3,354,704 A | * | 11/1967 | Gloor | ........................... 73/796 |
| 4,568,063 A | * | 2/1986 | Gramlich | .................... 254/10.5 |
| 5,191,689 A | * | 3/1993 | Slesinski et al. | ........ 29/243.517 |
| 5,795,257 A | * | 8/1998 | Giese et al. | .................. 474/109 |
| 6,662,666 B2 | * | 12/2003 | Hasegawa | ..................... 73/831 |
| 6,679,124 B2 | | 1/2004 | Oliver | |

FOREIGN PATENT DOCUMENTS

CN  1991332  7/2007

* cited by examiner

*Primary Examiner*—Lisa M Caputo
*Assistant Examiner*—Octavia Davis
(74) *Attorney, Agent, or Firm*—RatnerPrestia

(57) ABSTRACT

A spring supported lower clamper for direct tensile test, comprising a lower connection member, a lower end cap for holding a sample, a lower chain for connecting the lower connection member with the lower end cap, and spring-type supporting provisions for supporting a broken-apart lower part of the sample formed during the tensile test and the lower end cap. During the tensile test, the sample, the lower end cap and the lower chain are supported by the spring-type supporting provisions. Thus the sample can be prevented from being broken abruptly when a tensile force in the sample reaches its maximum level, and the mechanical behavior after the maximum tensile force is reached can be measured.

3 Claims, 4 Drawing Sheets

SPRING SUPPORTED LOWER CLAMPER FOR DIRECT TENSILE TEST

TECHNICAL FIELD

The present invention relates to a clamping device used in direct tensile test of a brittle material, especially to a clamping device used in direct tensile test of rock for holding a sample.

BACKGROUND ART

Tensile strength is an important mechanical characteristic of a brittle material, such as rock. Conventionally, in a tensile test for directly test the tensile strength of rock, a test machine is used which comprises a sample clamping device as shown in FIG. 1. The clamping device is supported by a bottom frame of the test machine 1 and comprises an upper clamper and a lower clamper. Each of the upper and lower clampers comprises a connection member 12 or 2 connected with the test machine, an end cap 9 or 7 for holding a sample 8, and a chain 11 or 3 for connecting the connection member with the end cap. The lower clamper, for carry a part of the sample which is broken after test and the end cap 7, further comprises a supporting means composed of a rigid sleeve 4 and a backing plate 6. Connecting pins 10 and 5 are shown for attaching the chains 11 and 3 to the end caps 9 and 7 respectively. During the tensile test, there is a clearance between the backing plate 6 and a recessed sample-holding part of the lower end cap 7, and thus the rigid sleeve 4 cannot effectively support the weights of the backing plate 6 and the lower end cap 7 during the whole test. When a tensile force in the sample reaches its maximum or peak level, the sample is broken abruptly under the weights of a lower part of the sample (the part under a broken plane to be created in the sample), the lower end cap and the lower chain, and thus the mechanical behavior after the maximum or peak tensile force is reached cannot be measured.

SUMMARY OF INVENTION

An object of the present invention is to overcome the above shortage existed in the prior art by providing a spring supported lower clamper for direct tensile test which can directly measure the mechanical behavior of a brittle material, such as rock, after the maximum tensile force is reached.

To achieve the above object, the present invention provides a lower clamper for direct tensile test which is improved over the lower clamper of the prior art by substituting the rigid sleeve with a compression helical spring.

Specifically, the spring supported lower clamper for direct tensile test of the present invention comprises a lower connection member connected with a bottom frame of the test machine, a lower end cap for holding a sample, a lower chain for connecting the lower connection member with the lower end cap, and supporting means for supporting a broken-apart lower part of the sample formed during the tensile test and the lower end cap. The lower end cap comprises a recessed sample-holding part and a mounting part, and the supporting means comprises a compression helical spring. During the tensile test, the above components are assembled so that one end of the compression helical spring is connected with or in contact with the recessed sample-holding part, and another end of the compression helical spring is connected with or in contact with the bottom frame of the test machine. The mounting part of the lower end cap, the lower chain and the lower connection member are inserted into and surrounded by the compression helical spring. One end of the lower chain is connected with the lower end cap by a lower connecting pin, and another end of the lower chain is connected with the lower connecting member. By means of the restoring force of the compression helical spring, the sample and the lower end cap are always supported by the spring during the whole tensile test. In addition, thanks to the adaptability of the spring by lateral deformation, the uniformity and directionality of the tensile stress in the sample will not be affected.

When a smaller sample is to be tested, smaller upper and lower end caps should be used. In this case, if the outer periphery of the recessed sample-holding part of the lower end cap is smaller than the inner diameter of the compression helical spring, a supporting plate should be added into the supporting means. The supporting plate is formed with a through hole. The diameter of the through hole is larger than the outer periphery of the mounting part of the lower end cap, but smaller than the outer periphery of the recessed sample-holding part of the lower end cap and the inner diameter of the compression helical spring. One end of the compression helical spring is connected with or in contact with the supporting plate, and another end of the compression helical spring is connected with or in contact with the bottom frame of the test machine. The mounting part of the lower end cap extends through the through hole of the supporting plate and is connected with the lower chain. The mounting part of the lower end cap, the lower chain and the lower connection member are inserted into and surrounded by the compression helical spring. One end of the lower chain is connected with the lower end cap by a lower connecting pin, and another end of the lower chain is connected with the lower connecting member. The sample and the lower end cap are always supported by the spring via the supporting plate during the whole tensile test.

The present invention can obtain the following advantages over the prior art.

1. The supporting means comprises a compression helical spring or a combination of a compression helical spring and a supporting plate. Thus, during the whole tensile test, the sample, the lower end cap and the lower chain (as well as the supporting plate in the test of smaller sample) are always supported by the spring. In this way, the sample can be prevented from being broken abruptly when a tensile force in the sample reaches its maximum level, and the mechanical behavior of a brittle material, such as rock, after the maximum tensile force is reached can be measured by a test machine incorporating the spring supported lower clamper of the present invention.

2. The spring supported lower clamper of the present invention has a simple structure, can be assembled easily and used conveniently, and is cost effective.

BRIEF INTRODUCTION TO THE DRAWINGS

The present invention will be described in details with reference to the drawings in which.

Figure 1:
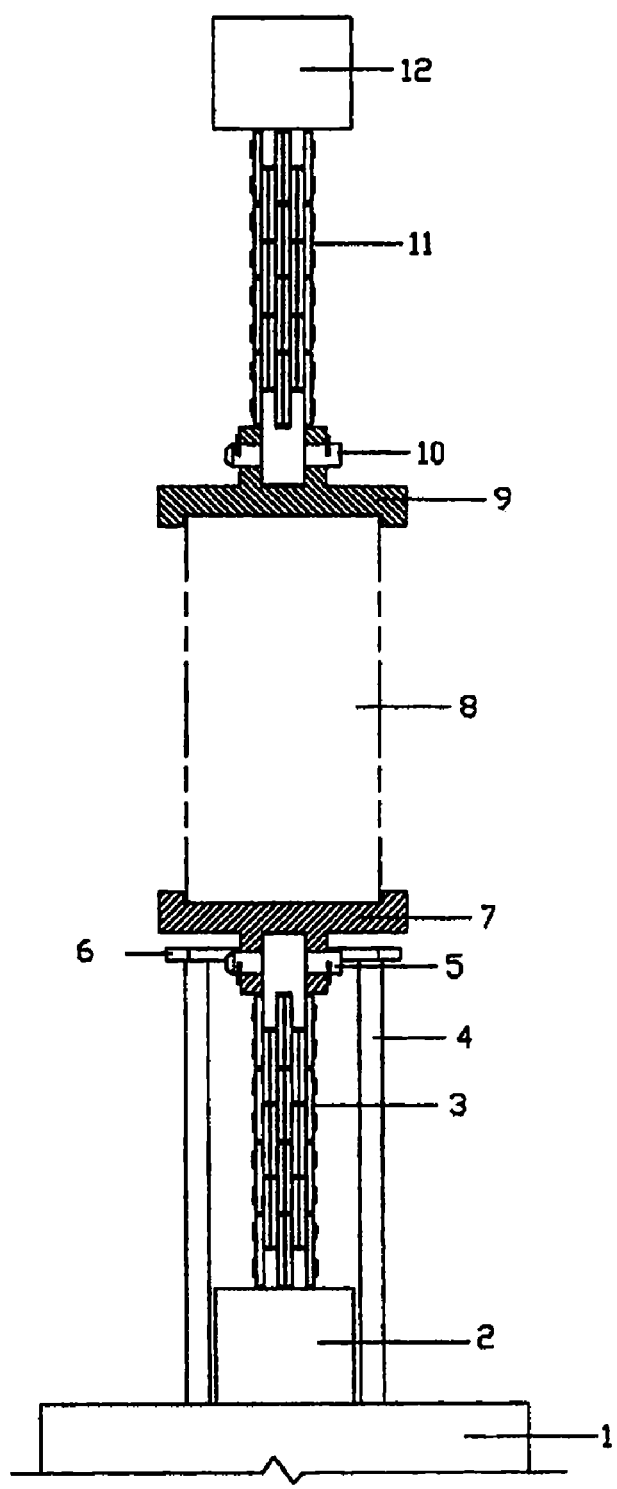
FIG. 1 is a schematic view showing the structure of conventional upper and lower clampers for direct tensile test and the mounting manner of a sample during tensile test.

Reference numerals appeared in the drawings include:
1—bottom frame of the test machine;
2—lower connection member;
3—lower chain;
4—sleeve;
5—lower connecting pin;
6—backing plate;
7—lower end cap;
8—sample;
9—upper end cap;
10—upper connecting pin;
11—upper chain;
12—upper connection member;
13—compression helical spring;
14—supporting plate
15—through hole

DETAILED DESCRIPTION OF THE PREFERRED EMBODIMENTS

First Embodiment of the Invention

Figure 2:
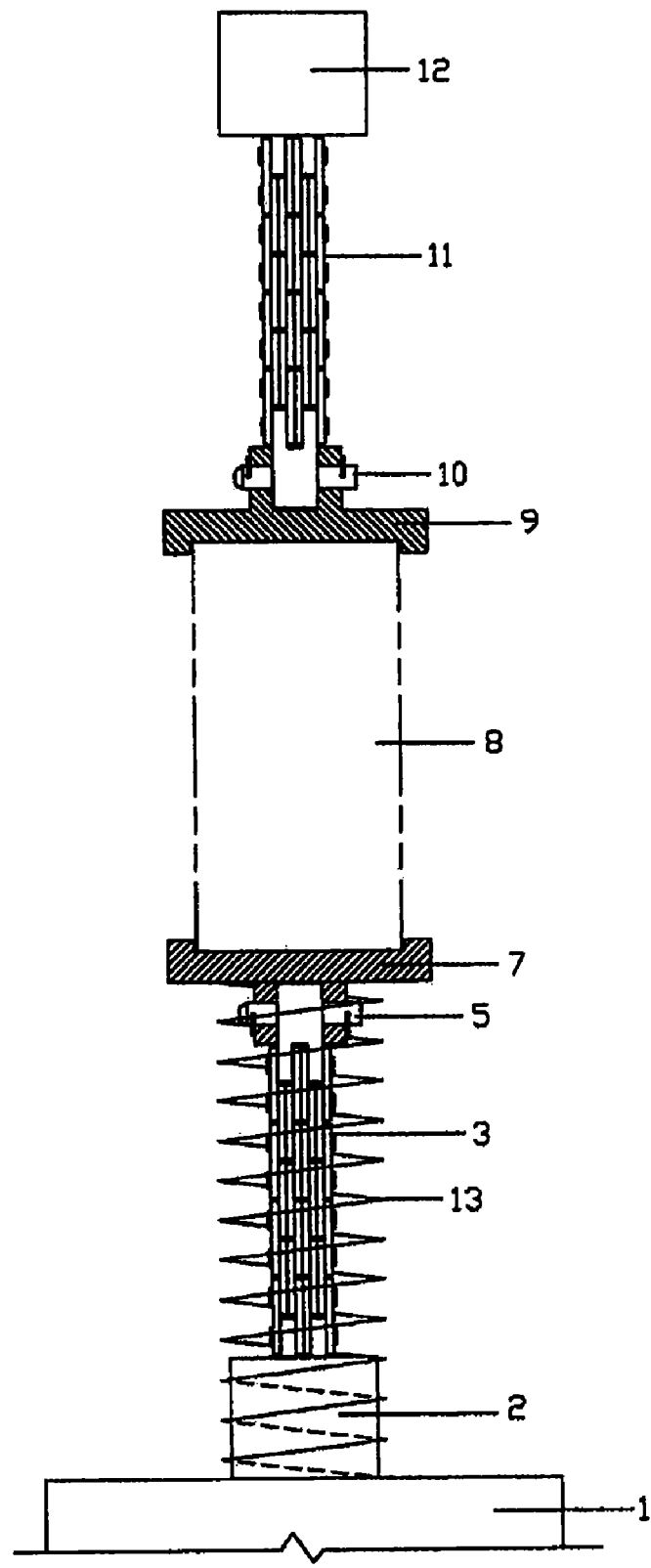
FIG. 2 is a schematic view showing the lower clamper for direct tensile test according to a first embodiment of the present invention as well as the structure of an upper clamper and the mounting manner of a sample during tensile test.

As shown in FIG. 2, the lower clamper for direct tensile test according to the first embodiment of the present invention comprises a lower connection member 2 connected with a bottom frame of the test machine 1, a lower end cap 7 for holding a sample 8, a lower chain 3 for connecting the lower connection member with the lower end cap, and supporting means for supporting a broken-apart lower part of the sample formed during the tensile test and the lower end cap. The supporting means comprises a cylindrical shaped compression helical spring 13. The free height $H_0$ of the compression helical spring (measured when the spring does not receive any load) is larger than the sum of the heights of the lower end cap, the lower chain and the lower connection member by about 3 cm to 6 cm. An initial compression ratio of the spring (i.e. the compression ratio of the spring when the spring is assembled) is about 15% to 25% of its free height $H_0$. The maximum allowable axial compression load of the spring is not lower than the sum of the weights of the sample, the lower connection member and the lower chain. The lower end cap 7 comprises a recessed sample-holding part and a mounting part which are formed integrally or connected together. The outer diameter of the recessed sample-holding part is larger than the outer diameter of the compression helical spring, while the outer diameter of the mounting part is smaller than the inner diameter of the compression helical spring. During the tensile test, the above components are assembled in the following way. Specifically, one end of the compression helical spring 13 is connected with or in contact with the bottom of the recessed sample-holding part, and another end of the compression helical spring 13 is connected with or in contact with the bottom frame of the test machine. The mounting part of the lower end cap 7, the lower chain 3 and the lower connection member 2 are inserted into and surrounded by the compression helical spring 13. One end of the lower chain 3 is connected with the lower end cap by a lower connecting pin 5, and another end of the lower chain 3 is connected with the lower connecting member 2.

The upper clamper comprises an upper connection member 12 connected with a top frame of the test machine, an upper end cap 9 for holding a sample 8, and an upper chain 11 for connecting the upper connection member with the upper end cap. During the tensile test, one end of the upper chain 11 is connected with the upper end cap by an upper connecting pin 10, and another end of the upper chain 11 is connected with the upper connection member 12.

The sample 8 is mounted in the test machine as shown in FIG. 2. The opposite ends of the sample are attached to the upper end cap 9 and the lower end cap 7 by highly adhesive glue.

Second Embodiment of the Invention

Figure 3:
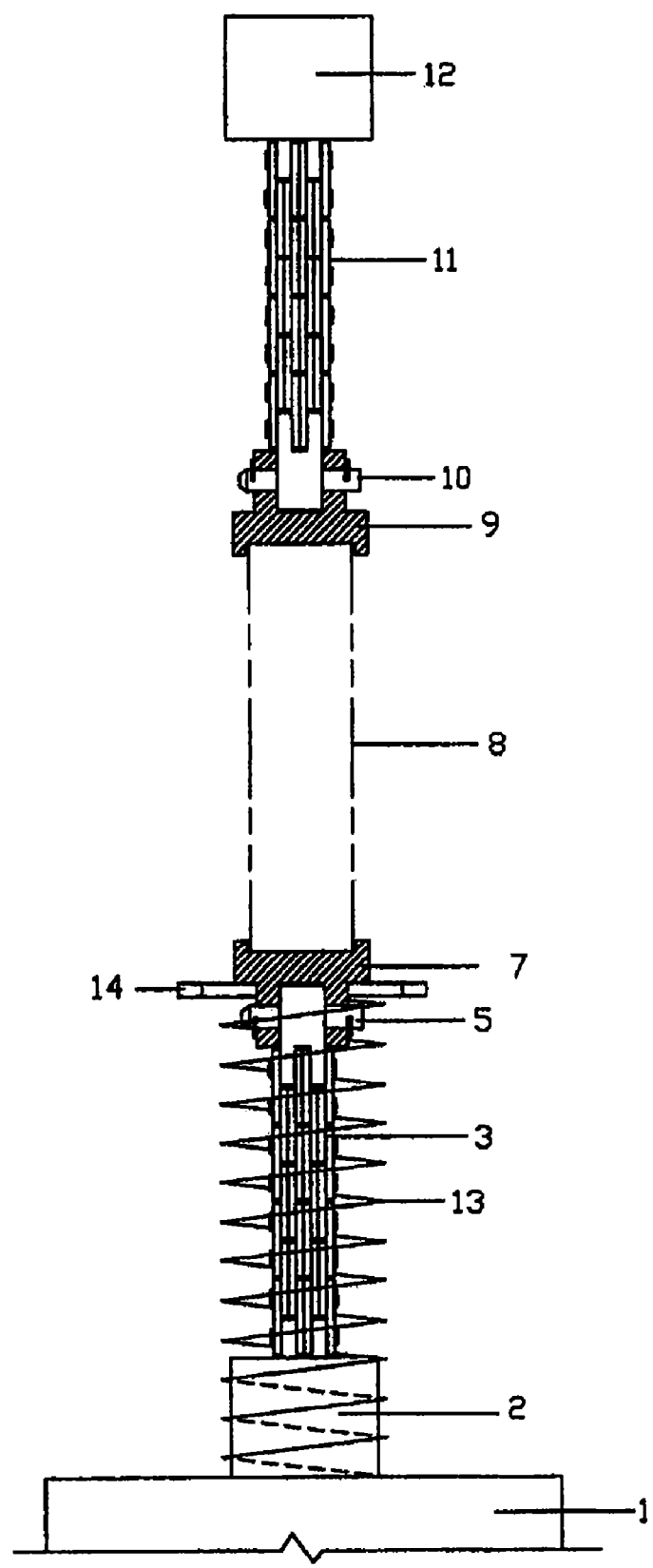
FIG. 3 is a schematic view showing the lower clamper for direct tensile test according to a second embodiment of the present invention as well as the structure of an upper clamper and the mounting manner of a sample during tensile test.
Figure 4:
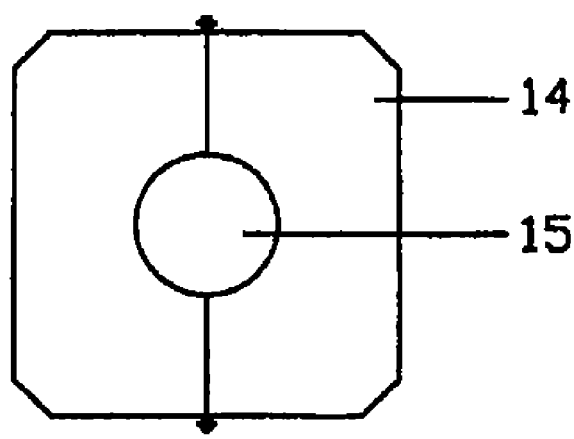
FIG. 4 is a schematic view of a supporting plate of the present invention.
Figure 5:
FIG. 5 is an end view of the supporting plate of FIG. 4.

As shown in FIG. 3, the lower clamper for direct tensile test according to the second embodiment of the present invention comprises a lower connection member 2 connected with a bottom frame of the test machine 1, a lower end cap 7 for holding a sample 8, a lower chain 3 for connecting the lower connection member with the lower end cap, and supporting means for supporting a broken-apart lower part of the sample formed during the tensile test and the lower end cap. The lower end cap 7 comprises a recessed sample-holding part and a mounting part which are formed integrally or connected together. The supporting means comprises a cylindrical shaped compression helical spring 13 and a supporting plate 14. Both the outer diameters of the recessed sample-holding part and the mounting part are smaller than the inner diameter of the compression helical spring. The free height $H_0$ of the compression helical spring (measured when the spring does not receive any load) is larger than the sum of the heights of the lower end cap, the lower chain and the lower connection member by about 3 cm to 6 cm. An initial compression ratio of the spring (i.e. the compression ratio of the spring when the spring is assembled) is about 15% to 25% of its free height $H_0$. The maximum allowable axial compression load of the spring is not lower than the sum of the weights of the sample, the lower connection member, the supporting plate and the lower chain. As shown in FIGS. 4 and 5, the supporting plate 14 are formed by two structurally symmetrical rectangular splitting plate-like members, and a through hole 15 is formed by two semi-circles in the splitting plate-like members and is located at the center of the supporting plate 14. The diameter of the through hole is larger than the outer diameter of the mounting part of the lower end cap 7, but smaller than the outer diameter of the recessed sample-holding part of the lower end cap 7 and the inner diameter of the compression helical spring. Each splitting plate-like member has a pair of lugs at the opposite ends of its splitting side. The splitting plate-like members are assembled together by the two pair of facing lugs. Preferably, one pair of the facing lugs are hinged together, and another pair of the facing lugs are connected by a screw. Alternatively, the two pair of facing lugs can by connected together by pins. During the tensile test, the above components are assembled in the following way. Specifically, one end of the compression helical spring 13 is connected with or in contact with the supporting plate 14, and another end of the compression helical spring 13 is connected with or in contact with the bottom frame of the test machine. The mounting part of the lower end cap 7 extends through the through hole 15 of the supporting plate and is connected with one end of the lower chain 3. Another end of the lower chain 3 is connected with the lower connecting member 2. The mounting part of the lower end cap 7, the lower chain 3 and the lower connection member 2 are inserted into and surrounded by the compression helical spring 13.

The structure of the upper clamper and the mounting manner of the sample 8 are shown in FIG. 3, and are similar to that in the first embodiment.

Figure 6:
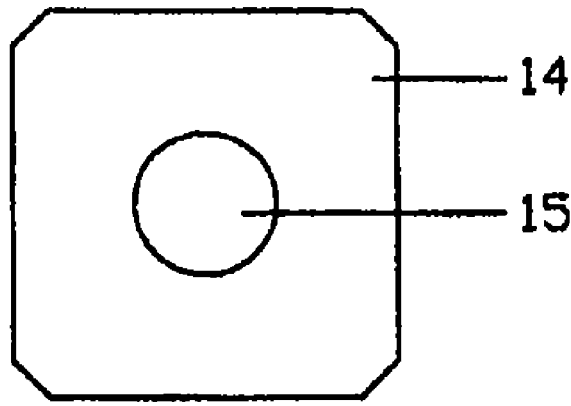
FIG. 6 is a schematic view of another supporting plate of the present invention.

The supporting plate 14 may also be an integral plate, with a through hole 15 formed at the center of it, as shown in FIG. 6.

What is claimed is:

1. A spring supported lower clamper for direct tensile test comprising a lower connection member connected with a bottom frame of the test machine, a lower end cap for holding a sample, a lower chain for connecting the lower connection member with the lower end cap, and supporting means for supporting a broken-apart lower part of the sample formed during the tensile test and the lower end cap, wherein the lower end cap comprises a recessed sample-holding part and a mounting part, the supporting means comprises a compression helical spring and a supporting plate which is formed with a through hole, the diameter of the through hole is larger than the outer periphery of the mounting part of the lower end cap, but smaller than the outer periphery of the recessed sample-holding part of the lower end cap and the inner diameter of the compression helical spring, the compression helical spring has one end connected with or in contact with the supporting plate and another end connected with or in contact with the bottom frame of the test machine, the mounting part of the lower end cap extends through the through hole of the supporting plate and is connected with the lower chain, and the mounting part of the lower end cap, the lower chain and the lower connection member are inserted into and surrounded by the compression helical spring.

2. The spring supported lower clamper of claim 1, wherein the supporting plate are formed by two structurally symmetrical splitting plate-like members, and a through hole is formed by two semi-circles in the splitting plate-like members and is located at the center of the assembled supporting plate.

3. The spring supported lower clamper of claim 1, wherein the supporting plate is an integral plate, with a through hole formed at the center of the supporting plate.

\* \* \* \* \*